United States Patent

(12) United States Patent
Lu (10) Patent No.: US 11,131,187 B2
(45) Date of Patent: Sep. 28, 2021

(54) IDENTIFYING HYDROCARBON PRODUCTION ZONES

(71) Applicant: Saudi Arabian Oil Company, Dhahran (SA)

(72) Inventor: Feng Hu Lu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 314 days.

(21) Appl. No.: 16/059,611

(22) Filed: Aug. 9, 2018

(65) Prior Publication Data

US 2019/0048717 A1    Feb. 14, 2019

Related U.S. Application Data

(60) Provisional application No. 62/545,280, filed on Aug. 14, 2017.

(51) Int. Cl.
| | | |
|---|---|---|
| E21B 49/08 | (2006.01) | |
| G01N 33/24 | (2006.01) | |
| G01K 3/14 | (2006.01) | |
| G01V 9/00 | (2006.01) | |

(52) U.S. Cl.
CPC ............ *E21B 49/087* (2013.01); *G01K 3/14* (2013.01); *G01N 33/24* (2013.01); *G01N 33/241* (2013.01); *G01V 9/007* (2013.01); *E21B 49/0875* (2020.05); *G01K 2003/145* (2013.01); *G01K 2213/00* (2013.01)

(58) Field of Classification Search
CPC ...... G01N 33/241; G01N 33/24; G01V 9/007; G01K 3/14; G01K 2213/00; G01K 2003/145; E21B 49/087; E21B 49/0875
See application file for complete search history.

(56) References Cited

U.S. PATENT DOCUMENTS

| | | | |
|---|---|---|---|
| 4,833,915 A | 5/1989 | Radd et al. | |
| 5,286,651 A | 2/1994 | Smith | |
| 5,328,849 A | 7/1994 | Smith | |

(Continued)

FOREIGN PATENT DOCUMENTS

| | | |
|---|---|---|
| CN | 104933281 | 9/2015 |
| CN | 105572131 | 5/2016 |

(Continued)

OTHER PUBLICATIONS

Gulf Cooperation Council Examination Report issued in GCC Application No. GC2018-35836 dated Jan. 14, 2020, 5 pages.

(Continued)

*Primary Examiner* — Nimeshkumar D Patel
*Assistant Examiner* — Gedeon M Kidanu
(74) *Attorney, Agent, or Firm* — Fish & Richardson P.C.

(57) ABSTRACT

A core sample with carbonate veins is obtained from a well formed in the hydrocarbon reservoir. Formation water samples are obtained from the well. Mineralogy of carbonate in the carbonate veins is analyzed. An oxygen isotope ratio between oxygen isotopes in the formation water and an oxygen isotope ratio between oxygen isotopes in the carbonates are determined. A formation paleo-temperature value is determined based on the determined oxygen isotope ratio using a model that relates the formation paleo-temperature value and the oxygen isotope ratio.

14 Claims, 5 Drawing Sheets

(56) References Cited

U.S. PATENT DOCUMENTS

| | | | |
|---|---|---|---|
| 5,416,024 | A | 5/1995 | Smith |
| 6,393,906 | B1 | 5/2002 | Vityk et al. |
| 9,128,076 | B2 | 9/2015 | Lamberti et al. |
| 9,470,665 | B2 | 10/2016 | Eisenhauer et al. |
| 2012/0215447 | A1 | 8/2012 | Lin |
| 2013/0037707 | A1* | 2/2013 | Lamberti ............ G01N 33/241 250/282 |
| 2016/0084817 | A1* | 3/2016 | Lawson ............... G01N 33/241 702/6 |
| 2016/0222782 | A1 | 8/2016 | Lawson et al. |
| 2016/0258922 | A1 | 9/2016 | Formolo et al. |
| 2017/0337302 | A1 | 11/2017 | Mezghani et al. |

FOREIGN PATENT DOCUMENTS

| | | |
|---|---|---|
| CN | 105930658 | 9/2016 |
| CN | 105930658 A * | 9/2016 |
| CN | 107218969 | 9/2017 |

OTHER PUBLICATIONS

Xi et al., "Diagenesis and reservoir quality of the Lower Cretaceous Quantou Formation tight sandstones in the southern Songlio Basin, China," Sedimentary Geology, Amsterdam, vol. 330, Oct. 30, 2015, 18 pages.

Horita, "Oxgen and carbon isotope fractionation in the system dolomite-water-CO2 to elevated temp," Geochimica et Cosmochimica Acta, vol. 129, Jan. 3, 2014, 14 pages.

International Search Report and Written Opinion issued in International Application No. PCT/US2018/046598 dated Dec. 14, 2018, 16 pages.

Friedman and O'Neil, "Chapter KK: Compilation of stable isotope fractionation factors of geochemical interest," in Data of Geochemistry, Sixth Edition, U.S. Geological Survey Professional Paper 440-kk, 1977, 117 pages.

Land, "Chapter 4: The Application of stable isotopes to studies of the origin of dolomite and to problems of diagenesis of clastic sediments," in Arthur et al., Stable Isotopes in Sedimentary Geology, Society of Economic Paleonotologiests and Mineralogists, Short Course No. 10, 1983, 75 pages.

Gulf Cooperation Council Examination Report issued in GCC Application No. GC2018-35836 dated Apr. 27, 2020, 5 pages.

Gulf Cooperation Council Examination Report in GCC Appln. No. GC2018-35836, dated Aug. 29, 2020, 4 pages.

* cited by examiner

IDENTIFYING HYDROCARBON PRODUCTION ZONES

CROSS-REFERENCE TO RELATED APPLICATIONS

This application claims the benefit of priority to U.S. Provisional Application Ser. No. 62/545,280, filed on Aug. 14, 2017, the entire contents of which are incorporated herein by reference.

TECHNICAL FIELD

This disclosure relates to oxygen isotope geothermometry.

BACKGROUND

Rocks and minerals formed million years ago, and have recorded geological environments, such as a paleo temperature. Carbonate veins formed during categenesis can have recorded information of geothermal events and petroleum cracking. Geochemical analysis of the vein carbonate minerals may reveal geothermal conditions existing at that time. For example, carbon and oxygen isotopes can help understand the origin of carbon in carbonate mineral and the temperature at which the carbonate was deposited.

SUMMARY

This disclosure describes technologies relating to identifying hydrocarbon production zones.

An example implementation of the subject matter described within this disclosure is a method with the following features. A core sample with carbonate veins is obtained from a well formed in the hydrocarbon reservoir. Formation water samples are obtained from the well. Mineralogy of carbonate in the carbonate veins is analyzed. An oxygen isotope ratio in the formation water and an oxygen isotope ratio in the carbonates are determined. A formation paleo-temperature value is determined based on the determined oxygen isotope ratio using a model that relates the formation paleo-temperature value and the oxygen isotope ratio.

Aspects of the example implementation, which can be combined with the example implementation alone or in combination, include the following. The core sample is a first core sample. The well is a first well formed at a first location in the hydrocarbon reservoir. The formation paleo-temperature value is a first formation paleo-temperature value. Multiple core samples are obtained, each with one or more carbonate veins, from a respective number wells formed at respective, different locations in the hydrocarbon reservoir. The core samples include the first core sample. The wells include the first well. For each core sample, a respective formation paleo-temperature is determined based on a respective oxygen isotope ratio in formation water samples obtained from each respective well and a respective oxygen isotope ratio in carbonates in carbonate veins in each core sample resulting in a plurality of formation paleo-temperature values. A three-dimensional formation paleo-temperature map of the hydrocarbon reservoir is generated based on the plurality of formation paleo-temperature values and the formation paleo-temperature value.

Aspects of the example implementation, which can be combined with the example implementation alone or in combination, include the following. A maturity of the hydrocarbon reservoir and sweet spots in the hydrocarbon reservoir for hydrocarbon production are determined based on the formation paleo-temperature map.

Aspects of the example implementation, which can be combined with the example implementation alone or in combination, include the following. Analyzing mineralogy of carbonate in the carbonate veins includes determining a presence of dolomite or calcite in the core sample.

Aspects of the example implementation, which can be combined with the example implementation alone or in combination, include the following. The carbonate is dolomite. Determining the formation paleo-temperature value based on the measured oxygen isotope ratios using a model that relates the formation paleo-temperature value and O-isotopes includes determining the formation paleo-temperature using the following equation:

$$10^3 \ln\alpha_{dolomite-water} = 3.14 \times 10^6 T^{-2} - 3.14$$

where, "T" is formation paleo-temperature, and "$\alpha_{dolomite-water}$" is the oxygen isotope fractionation between dolomite and water.

Aspects of the example implementation, which can be combined with the example implementation alone or in combination, include the following. The carbonate is calcite, and wherein determining the formation paleo-temperature value based on the measured oxygen isotope ratios using a model that relates the formation paleo-temperature value and O-isotopes includes determining the formation paleo-temperature using the following equation:

$$10^3 \ln\alpha_{calcite-water} = 2.789 \times 10^6 T^{-2} - 2.89$$

where, "T" is formation paleo-temperature, and "$\alpha_{dolomite-water}$" is the oxygen isotope fractionation between calcite and water.

Aspects of the example implementation, which can be combined with the example implementation alone or in combination, include the following. The oxygen isotope ratio of vein carbonate in the core sample is measured using an isotope ratio mass spectrometer.

Aspects of the example implementation, which can be combined with the example implementation alone or in combination, include the following. The well is purged prior to obtaining the formation water sample.

Aspects of the example implementation, which can be combined with the example implementation alone or in combination, include the following. Purging the well includes flowing water multiple times out of the well.

Aspects of the example implementation, which can be combined with the example implementation alone or in combination, include the following. Fluid inclusion is extracted from vein carbonate to obtaining the formation water sample.

Aspects of the example implementation, which can be combined with the example implementation alone or in combination, include the following. Oxygen isotopes of the formation water are analyzed.

Aspects of the example implementation, which can be combined with the example implementation alone or in combination, include the following. A location from which the core sample was obtained is determined not to be a gas sweet spot based on the formation paleo-temperature being less than 100 degrees Centigrade (° C.) or greater than 350° C.

Aspects of the example implementation, which can be combined with the example implementation alone or in combination, include the following. The hydrocarbon reservoir is an oil reservoir. A location from which the core sample was obtained is determined to be an oil sweet spot based on the formation paleo-temperature being substantially 100° C. The term "substantially" contemplates a variance of +/−5% from the mentioned numerical value.

Aspects of the example implementation, which can be combined with the example implementation alone or in combination, include the following. The hydrocarbon reservoir is a gas reservoir. A location from which the core sample was obtained is determined to be a gas sweet spot based on the formation paleo-temperature being between 150° C. and 250° C.

Aspects of the example implementation, which can be combined with the example implementation alone or in combination, include the following. Based on the formation paleo-temperature, the core sample is determined to have been obtained from a sweet spot in the hydrocarbon reservoir. Hydrocarbons are produced from a portion of the hydrocarbon reservoir from which the core sample was obtained.

An example implementation of the subject matter described within this disclosure is a computer implemented method performed by one or more processors for automatically selecting at least one service for use with a modeled user interface (UI) with the following features. A three-dimensional formation paleo-temperature map of a hydrocarbon reservoir is generated based on formation paleo-temperature values and sample locations. A location of a sweet spot in the hydrocarbon reservoir is determined based on the three-dimensional formation paleo-temperature map.

Aspects of the example computer implemented method, which can be combined with the example computer implemented method alone or in combination, include the following. A temperature value is generated based on a quantitative model utilizing oxygen isotopes of vein carbonate and formation water.

An example implementation of the subject matter described within this disclosure is a method with the following features. A core sample with carbonate veins is obtained from a well formed in the hydrocarbon reservoir. Formation water samples are obtained from the well. Mineralogy of carbonate in the carbonate veins is analyzed. An oxygen isotope ratio in the vein carbonates and an oxygen isotope ratio in a fluid inclusion within the vein carbonates is determined. A formation paleo-temperature value is determined based on the determined oxygen isotope ratio using a model that relates the formation paleo-temperature value and the oxygen isotope ratio.

An example implementation of the subject matter described within this disclosure is a method with the following features. Formation water samples are obtained by extracting fluid inclusion from vein carbonate from the well. A core sample with carbonate veins from a well formed in the hydrocarbon reservoir is obtained. Mineralogy of carbonate in the carbonate veins is analyzed. An oxygen isotope ratio in the vein carbonates and an oxygen isotope ratio in a fluid inclusion within the vein carbonates are determined. A formation paleo-temperature value is determined based on the determined oxygen isotope ratio using a model that relates the formation paleo-temperature value and the oxygen isotope ratio.

The details of one or more implementations of the subject matter described in this disclosure are set forth in the accompanying drawings and the description that follows. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Thermal maturity is a parameter that can be used to assess unconventional shale gas potential. However, there are difficulties in determining maturity. This disclosure describes a method utilizing carbonate veins that formed during petroleum cracking to determine paleo temperature and maturity, and to help identify gas sweet spots. Carbonate veins can include dolomite and calcite, which may have formed, for example, at different temperatures or at different geological times or both. Geochemical analysis of carbonates can help reconstruct paleo environments at which carbonate minerals were deposited. Carbon and oxygen isotopes of carbonates have been widely utilized to determine change in climate and paleo temperature. Particularly oxygen isotope ratios, such as $O^{18}$ and $O^{16}$, are sensitive to temperature change. The oxygen isotope ratios can correlate to a formation paleo-temperature, that is, a temperature of the formation at which the carbonate was formed. Paleo-temperatures can be used to determine a maturity of hydrocarbons within a source rock or reservoir. For example, at certain temperatures, kerogen/organic-matter cracks and generates heavier hydrocarbons, such as crude-oil or condensates, while at comparatively greater temperatures, the kerogen/organic-matter can further breakdown and crack kerogen and heavy hydrocarbons, leading to dry natural gas formations.

This disclosure discusses a method of characterizing paleo-temperatures at which petroleum cracking and vein carbonate precipitation within fractures occurs in a reservoir or source-rock based upon ratios of oxygen isotopes within the vein carbonates and formation water. The method includes obtaining a core sample with carbonate veins from an exploration and production well, identifying the mineralogy of the carbonate, extracting formation water from a fluid inclusion within the same vein carbonate, analyzing the oxygen and carbon isotopes within the vein carbonates, analyzing oxygen isotopes in fluid inclusions within the vein carbonates, determining the formation paleo-temperature based on the measured isotope ratios and disclosed equations, mapping the distribution of paleo-temperatures, and determining maturity and sweet spots for hydrocarbon production based on the developed map. A sweet spot is generally defined in this disclosure as the area within a reservoir that represents the best production or potential for production. Alternatively, oxygen isotopes in collected formation water can be analyzed if oxygen isotope analysis in fluid inclusions is not available. The described method can be applied to both conventional reservoirs and unconventional shale gas reservoirs.

Figure 1A:
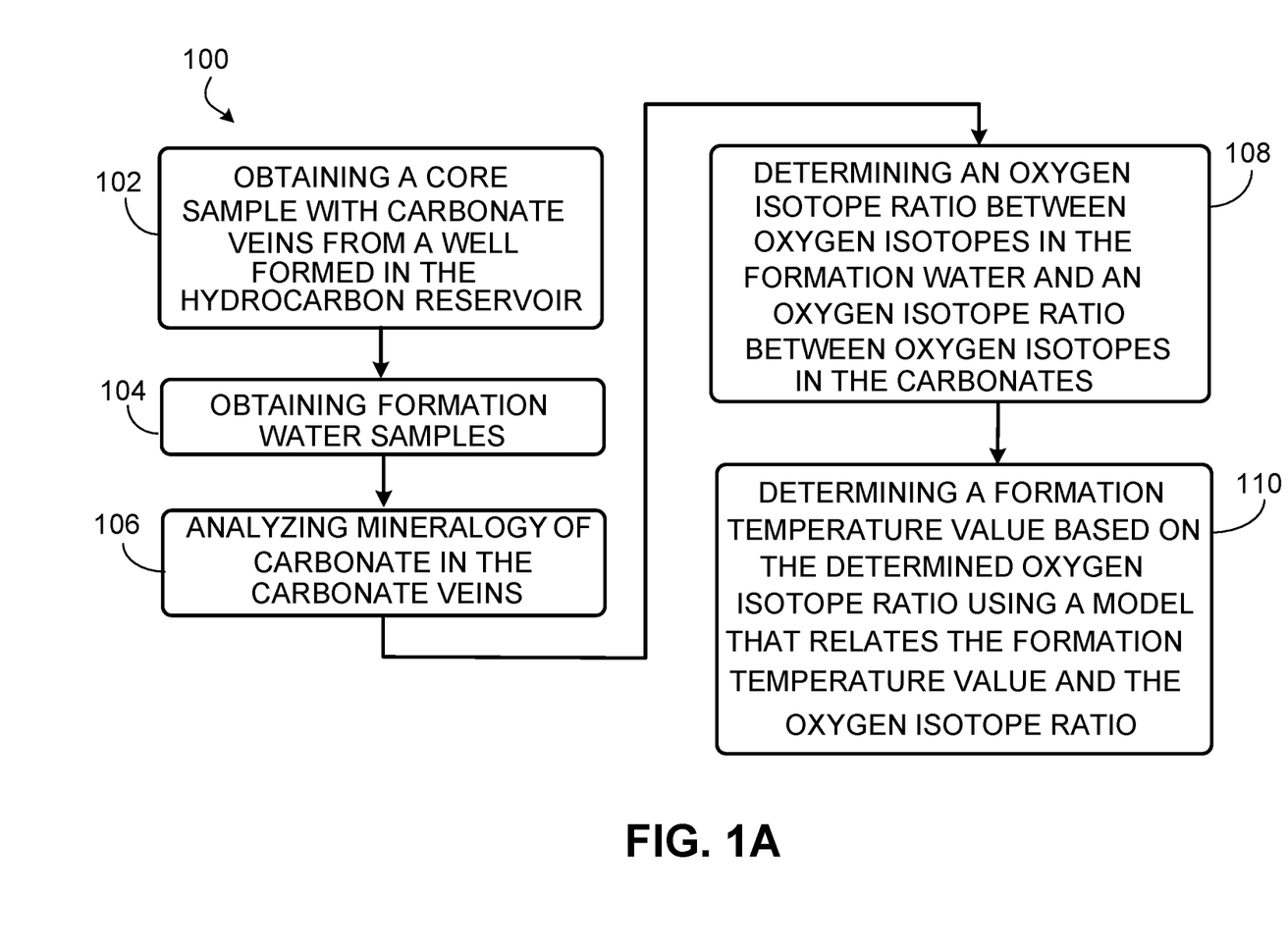
FIGS. 1A-1B is a flowchart of an example method that can be used to determine a paleo-temperature within a geologic formation.

FIG. 1A shows a flowchart of an example method 100 to determine a paleo-temperature that occurred within a reservoir. At 102, a carbonate vein sample is obtained from a core sample from a wellbore formed in the targeted hydrocarbon reservoir or source rock. The core sample can be obtained with a coring bit or with any other coring apparatus Carbonate vein samples can be located because exploration wells may have been previously drilled, and samples from targeted formations may have been cored, collected, studied, and published. If the cored samples contain carbonate veins, rocks from the same formation can contain similar carbonate veins. Veins are carbonates that have precipitated in fractures. Fractures can be formed by tectonic and structural activities and by petroleum cracking, that is, gas formation increases pressure and creates fractures. Such fractures can be distributed all over the basin and formation because of similar geological conditions. In some instances, fractures and veins can be observed from outcrops, if there are any outcrops in the basin.

Figure 1B:
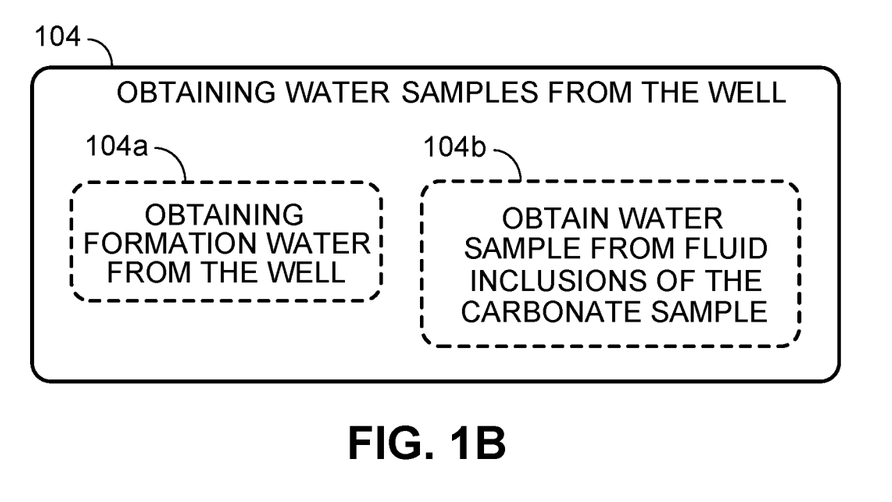

At 104, water samples are obtained from the same well in which the vein sample is obtained. FIG. 1B shows two possible methods for obtaining the water samples. At 104a, modern water is obtained from the well. In some implementations, the well can be purged prior to obtaining the formation water sample. Purging the well can include flowing volumes water multiple times out of the well prior to collecting the water sample. During the process of well drilling and development, drilling fluids are utilized and injected into the well and formation. After the well is drilled to the targeted depth and width, injected fluids can be pumped out in order to sample uncontaminated formation water. Formation water can be collected to measure parameters in the reservoir, such as salinity, pH value, temperature, to name a few. In some instances, three to five times the well-volumes of water are pumped out of the well before a water sample is collected. Such a sample can be an accurate representation of the fresh formation reservoir water. The water samples can be obtained by pumping the water from the wellbore interval in which the core-sample was obtained to a topside facility. In some implementations, the water samples can be stored in brown glass bottles with Teflon liner caps. The bottles can be filled full without any headspace. The bottles can be 20 milliliters (ml), 40 ml, 100 ml, or any other size that contains enough fluid for testing. The water samples can be stored at −4° C. In some implementations, the water samples do not come into contact with ambient air. Any evaporation of water can vary isotope composition. In some implementations, water samples can be collected and O-isotopes from the water can be analyzed in order to analyze O-isotopes from fluid inclusions (water) within the same carbonate veins to be used and analyzed for C- and O-isotopes.

The O-isotope ratios from the two materials (vein carbonate and formation water) can be used to determine a paleo-temperature. The previously mentioned water sampling collects modern formation water, which may not represent paleo formation water. At 104b, oxygen isotope from fluid inclusion within the vein carbonates are directly analyzed and are used to analyze O-isotopes. In such an implementation, the fluid is the formation water preserved in carbonate while carbonate mineral was precipitating. For example, a vein carbonate sample is placed in a vacuumed container, which is directly heated up to 400° C., water vapor is collected in a tube in a cryogenic trap. The tube is connected to the sample heating container. Then water is transferred from the tube to a vial capped with septum and analyzed for O-isotope ratio using an isotope ratio mass spectrometer.

Returning to FIG. 1A, at 106, a mineralogy of carbonate in the carbonate veins is analyzed. Analyzing mineralogy of carbonate in the carbonate veins can include determining a presence of dolomite or calcite within the core sample. There are many ways to determine carbonate mineralogy. For example, X-ray Diffraction (XRD) and Scanned Electron Microscopy (SEM) can be used. To determine carbonate minerals, XRD can be used to analyze carbonate powder samples. If the vein samples are too small for X-ray analysis, SEM is used to examine a thin section of the sample which includes a rock slab with a carbonite vein. SEM with half quantitative analysis is able to tell calcite from dolomite.

At 108, an oxygen isotope ratio is determined in both the formation water and the carbonates, respectively. For example, during the oxygen isotope analysis, the values of $O_{18}/O_{16}$ ratios, in carbonate and water are calibrated with two or more international oxygen isotope standards. The values of $O_{18}/O_{16}$ are expressed as per million or per thousand. The isotope ratios in water and carbonates vary considerably. For example, the isotope ratio in formation water can range from −10 to +10 per-million, while in vein carbonates the isotope ratio can range from −20 to +20 per-million. In some implementations, a ratio of carbon isotopes in vein carbonate can be determined as well. The carbon isotope ratios can be checked to corroborate the determined oxygen isotope ratio. For example, the carbon isotopes can be used to determine if $CO_2$ has been produced from hydrocarbon cracking. That is, C-isotopes are used to determine the origin of $CO_2$ (which forms carbonates). For example, $CO_2$ can be derived from either dissolution of old carbonates, or organic matter degradation and cracking. In some implementations, the oxygen isotope ratio of vein carbonates in the core sample can be measured using an isotope ratio mass spectrometer (IRMS), or any other measuring device capable of determining oxygen isotope ratios. In some implementations, individual isotopes are not measured, rather, only the ratio is measured and calibrated with that of international standards. In such an implementation, any systematic error can be cancelled by the ratio. Therefore, O-isotope ratio of one sample will be measured with a same or quite similar result regardless of where the sample in analyzed using similar instruments.

At 110, a formation paleo-temperature value is determined based on the determined oxygen isotope ratio in the vein carbonate and on the determined oxygen isotope ratio in the formation water using a model that relates the formation paleo-temperature value and the oxygen isotope ratio.

In some instances, the vein carbonate is dolomite. In such an instance, determining the formation paleo-temperature value based on the measured oxygen isotope ratios can include using the following equation:

$$10^3 \ln\alpha_{dolomite-water} = 3.14 \times 10^6 T^{-2} - 3.14 \quad \text{(Eq. 1)}$$

In Eq. 1, "T" is a formation paleo-temperature, and "$\alpha_{dolomite-water}$" is the oxygen isotope fractionation factor between dolomite and water.

In some instances, the vein carbonate is calcite. In such an instance, determining the formation paleo-temperature value based on the measured oxygen isotope ratios can include using the following equation:

$$10^3 \ln\alpha_{calcite-water} = 2.789 \times 10^6 T^{-2} - 2.89 \quad \text{(Eq. 2)}$$

In Eq. 2, "T" is a formation paleo-temperature, and "$\alpha_{calcite-water}$" is the oxygen isotope fractionation factor between calcite and water.

Figure 2:
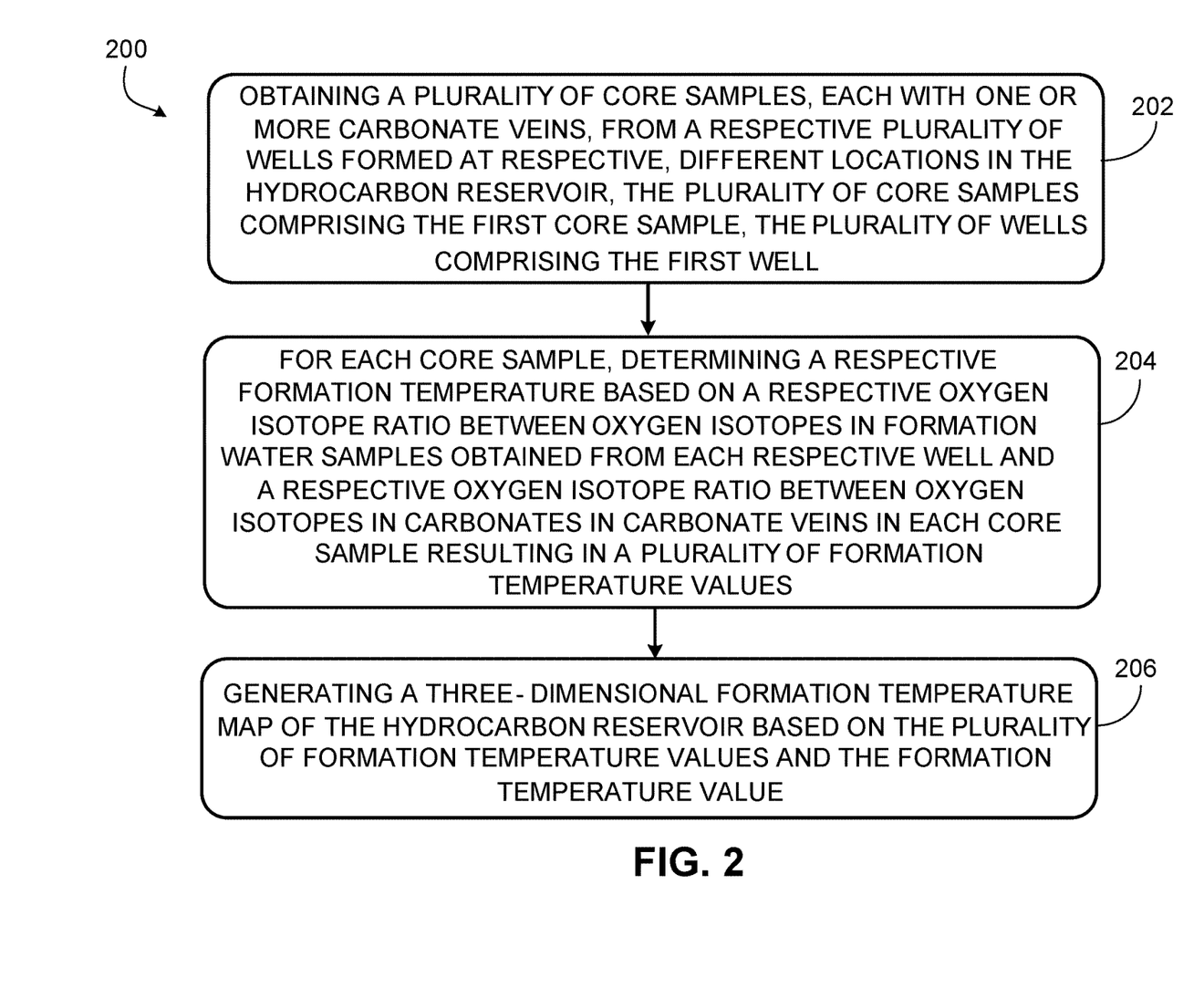
FIG. 2 is a flowchart of an example method of mapping variation of paleo-temperature in a reservoir using oxygen isotope ratios.

FIG. 2 shows a flowchart of a second method 200 that can be used in conjunction with the method 100 to determine a paleo-temperature distribution within a geologic formation. In the second method 200, additional core samples are taken from additional wells formed within the same geologic formation. At 202, multiple core samples are obtained. Each of the core samples has carbonate veins from a respective well formed at respective, different locations in the geologic formation. The core samples can include the first core sample previously described, and the wells can include the first well previously described. At 204, for each vein carbonate sample, a respective formation paleo-temperature is determined based on a respective set of oxygen isotope ratios measured from vein carbonate and formation water collected from each well. Multiple paleo temperature values can be obtained from each of the respective multiple wells from the same formation in the same petroleum basin. In some implementations, the samples can be collected from the same formation or reservoir, but the depth of the same formation can vary from one location (well) to another (well). Collecting samples at different depths of the same formation can allow determining different paleo-temperatures in the same formation. The respective paleo-temperatures can be determined by implementing the method 100 described in FIGS. 1A-1B. At 206, a three-dimensional formation paleo-temperature map of the hydrocarbon reservoir is generated based on the plurality of formation paleo-temperature values and the locations from which each of the core samples were taken. The generated three-dimensional map can be used to help plan the wellbore routes of future exploration and production wells.

Figure 3:
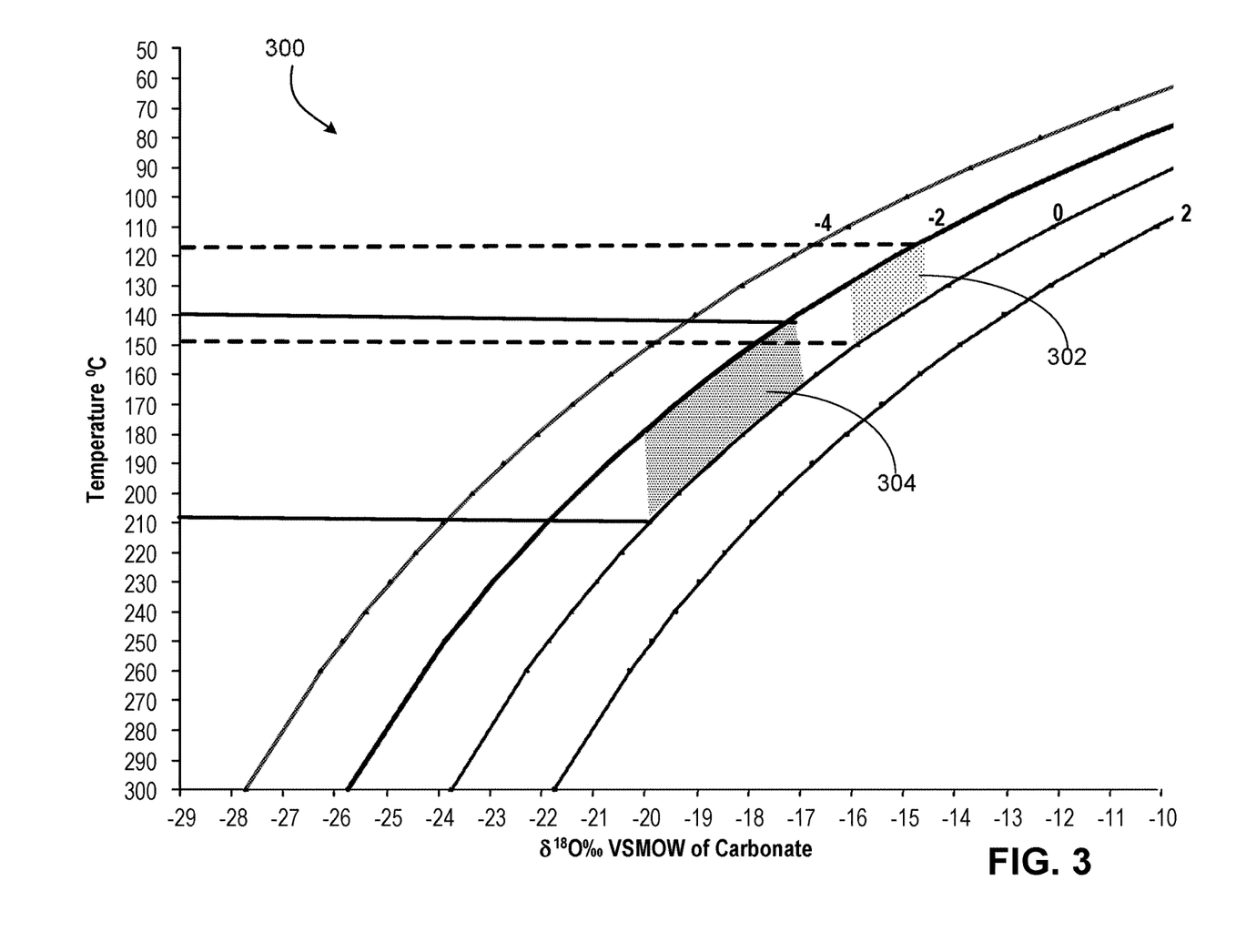
FIG. 3 is a graph of an example correlation between oxygen isotopes and formation paleo-temperature.

A maturity of the hydrocarbon reservoir and sweet spots in the hydrocarbon reservoir for hydrocarbon production can be determined based on the formation paleo-temperature map. An example of correlations that can be used to determine potential sweet spots is shown in FIG. 3 with graph 300. The graph 300 shows a first highlighted region 302 and a second highlighted region 304. The first highlighted region 302 is indicative of oil formation within a geologic formation, while the second region 304 is indicative of gas formation within the geologic formation.

For example, based on the graph 300, it can be determined that a location from which a core sample was obtained is not a gas sweet spot based on the formation paleo-temperature being less than 100° C. That is, paleo temperatures less than 100° C. are on the outer edge of both the first highlighted region 302 and the second highlighted region 304. At greater temperatures, for example, greater than 350° C., any hydrocarbons present in the geologic formation can be "cooked" to a point where the hydrocarbons are destroyed. Less than 100° C., natural gas within a geologic formation does not viably form. In another example, the hydrocarbon reservoir can be an oil reservoir. At greater temperatures, such as 150° C.-250° C., kerogen and oil can be cracked to dry gas and produce a viable gas reservoir. That is, the formation paleo-temperature falls within the first highlighted region 302. In another example, the hydrocarbon reservoir can be a gas reservoir. A location from which the core sample was obtained can be determined to be a sweet spot based on the formation paleo-temperature being between 150° C. and 250° C. That is, the formation paleo-temperature falls within the second highlighted region 304. A "sweet spot" is a 3-D location. For example, a formation or reservoir can be two-hundred meters (m) thick. Based on temperature modeling, the interval between 100-150 m can have a paleo-temperature between 150° C.-250° C. In such an instance, that interval can be a sweet spot from a vertically depth perspective. In this example, there can be three wells, well A, well B, and well C. The three wells can be considered point of a triangle. If all three wells have a paleo-temperature between 150° C.-250° C. and are located within the same formation, then any spot in the middle of the triangle between A, B, C wells can be a potential sweet spot. After determining that a core sample is obtained from a sweet spot in the hydrocarbon reservoir, hydrocarbons can be produced from the portion of the hydrocarbon reservoir from which the core sample was obtained. The lines with values represent water O-isotope values. O-isotope values in both water and carbonates constrain the range of temperature. Two blocks as marked 302 and 304 are for calcite and dolomite respectively. Each block has a range, one data from one well counts only one point within each block. Temperatures indicative of potential sweet spots can vary somewhat between formations. For example, the temperature ranges of 150-250° C., 140-240° C., or 160-260° C. can all be indicative of a potential sweet spot in certain instances.

Implementations of the subject matter described in this disclosure can be implemented in a computing system that includes a back-end component, such as, as a data server, or that includes a middleware component, such as, an application server, or that includes a front-end component, such as, a client computer having a graphical user interface or a Web browser through which a user can interact with an implementation of the subject matter described in this disclosure, or any combination of one or more such back-end, middleware, or front-end components. The components of the system can be interconnected by any form or medium of digital data communication, such as, a communication network. Examples of communication networks include a local area network ("LAN") and a wide area network ("WAN"), an inter-network (such as, the Internet), and peer-to-peer networks (such as, ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (such as, an HTML page) to a client device (such as, for purposes of displaying data to and receiving user input from a user interacting with the client device). Data generated at the client device (such as, a result of the user interaction) can be received from the client device at the server.

Figure 4:
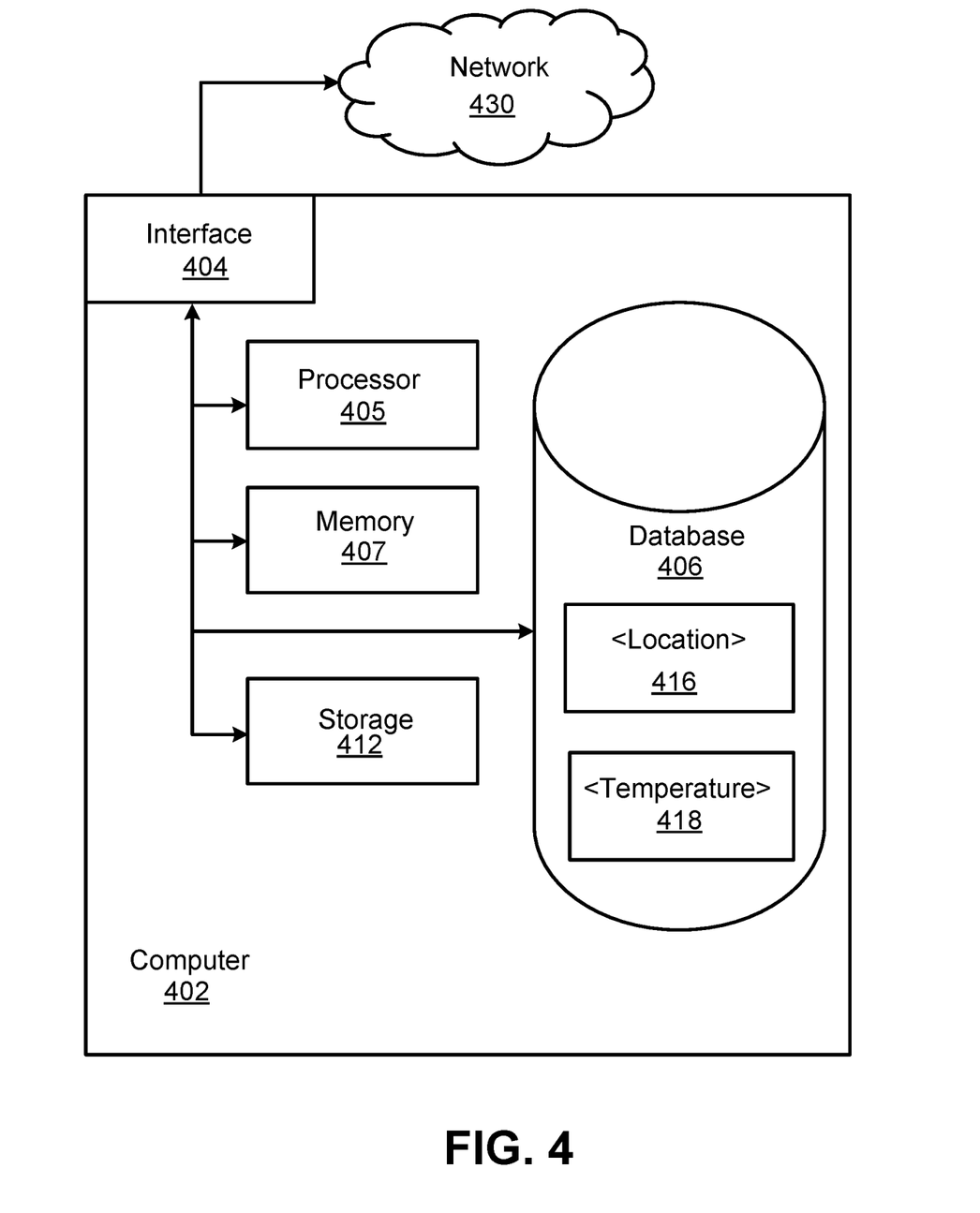
FIG. 4 is a schematic diagram of a general purpose computer that can be used in conjunction with the subject matter within this disclosure.

An example of one such type of computer is shown in FIG. 4, which shows a block diagram of a programmable computer 402 suitable for performing methods of various aspects of the subject matter described in this disclosure. The computer 402 includes a processor 405, memory 407, (for example, a writable read-only memory (ROM) such as a flash ROM, or random access memory (RAM)), and a storage medium 412. The computer 402 can be preprogrammed, in ROM, for example, or it can be programmed (and reprogrammed) by loading a program from another source (for example, from a floppy disk, a CD-ROM, a flash drive, or another computer).

The storage medium 412 suitable for storing executable computer programs, such as a hard disc drive or solid state drive, can include programs embodying aspects of the subject matter described in this disclosure, and data, such as a 3D paleo-temperature distribution map.

The computer 402 can receive and transmit data (for example, stills, pictures, movies and animations for importing into a composition) in analog or digital form over an interface 404. The interface 404 can include any communication links such as a serial link, local area network, wireless link, and parallel link. The interface 404 can allow the computer to connect to a network 430 that can include a communication network. Examples of communication networks include a local area network ("LAN") and a wide area network ("WAN"), an inter-network (such as, the Internet), and peer-to-peer networks (such as, ad hoc peer-to-peer networks).

Data used by the computer 402 can be stored locally or on a remote server within a database 406 that can include various datatypes used in implementations of the methods described within this disclosure. For example, the database can include a location datatype 416, a paleo-temperature datatype 418, to name a few.

While this disclosure contains many specific implementation details, these should not be construed as limitations on the scope of any inventions or of what may be claimed, but rather as descriptions of features specific to particular implementations of particular inventions. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described earlier as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described earlier should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method of determining a paleo-temperature of a hydrocarbon reservoir, the method comprising:
    obtaining a core sample with carbonate veins from a well formed in the hydrocarbon reservoir;
    obtaining formation water samples from the well;
    analyzing mineralogy of carbonate in the carbonate veins;
    determining an oxygen isotope ratio in the formation water samples from the well and an oxygen isotope ratio in the carbonates;
    determining a formation paleo-temperature value based on the determined oxygen isotope ratio using a model that relates the formation paleo-temperature value and the oxygen isotope ratio;
    based on the formation paleo-temperature, determining that the core sample was obtained from a sweet spot in the hydrocarbon reservoir; and
    producing hydrocarbons from a portion of the hydrocarbon reservoir from which the core sample was obtained.

2. The method of claim 1, wherein analyzing mineralogy of carbonate in the carbonate veins comprises determining a presence of dolomite or calcite in the core sample.

3. The method of claim 1, wherein the carbonate is dolomite, and wherein determining the formation paleo-temperature value based on the measured oxygen isotope ratios using a model that relates the formation paleo-temperature value and 0- isotopes comprises determining the formation paleo-temperature using the following equation:

$$10^3 \ln\alpha_{dolomite-water} = 3.14 \times 10^6 T^{-2} - 3.14,$$

wherein, "T" is formation paleo-temperature, and "$\alpha_{dolomite-water}$" is the oxygen isotope fractionation between dolomite and water.

4. The method of claim 1, wherein the carbonate is calcite, and wherein determining the formation paleo-temperature value based on the measured oxygen isotope ratios using a model that relates the formation paleo-temperature value and 0- isotopes comprises determining the formation paleo-temperature using the following equation:

$$10^3 \ln\alpha_{calcite-water} = 2.789 \times 10^6 T^{-2} - 2.89,$$

wherein, "T" is formation paleo-temperature, and "$\alpha_{calcite-water}$" is the oxygen isotope fractionation between calcite and water.

5. The method of claim 1, further comprising measuring the oxygen isotope ratio of vein carbonate in the core sample using an isotope ratio mass spectrometer.

6. The method of claim 1, further comprising determining that a location from which the core sample was obtained is not a gas sweet spot based on the formation paleo-temperature being less than 100° C. or greater than 350° C.

7. The method of claim 1, wherein the hydrocarbon reservoir is an oil reservoir, and wherein the method further comprises determining that a location from which the core sample was obtained is an oil sweet spot based on the formation paleo-temperature being substantially 100° C.

8. The method of claim 1, wherein the hydrocarbon reservoir is a gas reservoir, and wherein the method further comprises determining that a location from which the core sample was obtained is a gas sweet spot based on the formation paleo-temperature being between 150° C. and 250° C.

9. The method of claim 1, wherein the core sample is a first core sample, the well is a first well formed at a first location in the hydrocarbon reservoir, the formation paleo-temperature value is a first formation paleo-temperature value, and wherein the method further comprises:
    obtaining a plurality of core samples, each with one or more carbonate veins, from a respective plurality of wells formed at respective, different locations in the hydrocarbon reservoir, the plurality of core samples comprising the first core sample, the plurality of wells comprising the first well;
    for each core sample, determining a respective formation paleo-temperature based on a respective oxygen isotope ratio in formation water samples obtained from each respective well and a respective oxygen isotope ratio in carbonates in carbonate veins in each core sample resulting in a plurality of formation paleo-temperature values; and generating a three-dimensional formation paleo-temperature map of the hydrocarbon reservoir based on the plurality of formation paleo-temperature values and the formation paleo-temperature value.

10. The method of claim 9, further comprising determining maturity of the hydrocarbon reservoir and sweet spots in the hydrocarbon reservoir for hydrocarbon production based on the formation paleo-temperature map.

11. The method of claim 1, further comprising purging the well prior to obtaining the formation water sample.

12. The method of claim 11, wherein purging the well comprises flowing water multiple times out of the well.

13. The method of claim 1, further comprising extracting fluid inclusion from vein carbonate to obtaining the formation water sample.

14. The method of claim 13, further comprising analyzing oxygen isotopes of the formation water.

\* \* \* \* \*

UNITED STATES PATENT AND TRADEMARK OFFICE
CERTIFICATE OF CORRECTION

PATENT NO. : 11,131,187 B2
APPLICATION NO. : 16/059611
DATED : September 28, 2021
INVENTOR(S) : Lu Page 1 of 1

It is certified that error appears in the above-identified patent and that said Letters Patent is hereby corrected as shown below:

In the Claims

Column 10, Line 18, Claim 3, delete "0- isotopes" and insert -- O- isotopes --;

Column 10, Line 29, Claim 4, delete "0- isotopes" and insert -- O- isotopes --.

Signed and Sealed this
Eighth Day of February, 2022

Drew Hirshfeld
*Performing the Functions and Duties of the
Under Secretary of Commerce for Intellectual Property and
Director of the United States Patent and Trademark Office*